US00PP20462P3

(12) United States Plant Patent
Blom

(10) Patent No.: US PP20,462 P3
(45) Date of Patent: Nov. 10, 2009

(54) ***CHRYSANTHEMUM* PLANT NAMED 'ZANMUGOLDRU'**

(50) Latin Name: *Chrysanthemum×morifolium*
Varietal Denomination: Zanmugoldru

(75) Inventor: Wilhelmus Bernardus Blom, GA Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/003,568

(22) Filed: Dec. 28, 2007

(65) Prior Publication Data

US 2009/0172852 P1 Jul. 2, 2009

(51) Int. Cl.
*A01H 5/00* (2006.01)

(52) U.S. Cl. ..... Plt./289

(58) Field of Classification Search ..... Plt./289
See application file for complete search history.

*Primary Examiner*—David H Kruse
*Assistant Examiner*—June Hwu
(74) *Attorney, Agent, or Firm*—Steptoe & Johnson LLP

(57) ABSTRACT

A *chrysanthemum* plant named 'Zanmugoldru' characterized by its small sized blooms with yellow ray florets and prolific branching; natural season flower date October 8 (week 41); blooming for a period of 5 weeks.

3 Drawing Sheets

Botanical designation: *Chrysanthemum×morifolium* Ramat.

Cultivar denomination: 'Zanmugoldru'.

BACKGROUND OF THE INVENTION

The present invention relates to a new and distinct cultivar of *chrysanthemum* plant, botanically known as *Chrysanthemum×morifolium* Ramat., commercially grown as a garden mum, and herein after referred to by the cultivar denomination 'Zanumgoldru'. 'Zanmugoldru' is a product of a breeding and selection program for outdoor pot mums (garden mums) which had the objective of creating new *chrysanthemum* cultivars with a double type flower, a natural season flower date around October 8 (week 41); blooming for a period of 5 weeks. 'Zanmugoldru' is a seedling resulting from a crossing of the seed parent id 995 and the pollen parent id 710. Plants of the new cultivar 'Zanmugoldru' differ from plants of the parents mainly in natural-season flowering (1) and flower color (2). (1) The plants of the seed parent flower in early season, while those of 'Zanmugoldru' in late season. (2) The flowers of the pollen parent are more pale yellow than those of 'Zanmugoldru'

The new and distinct cultivar was discovered and selected as a flowering plant by Wilhelmus Bernardus Blom on a cultivated field in Rijsenhout, The Netherlands in 2005. The first act of asexual production of 'Zanmugoldru' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
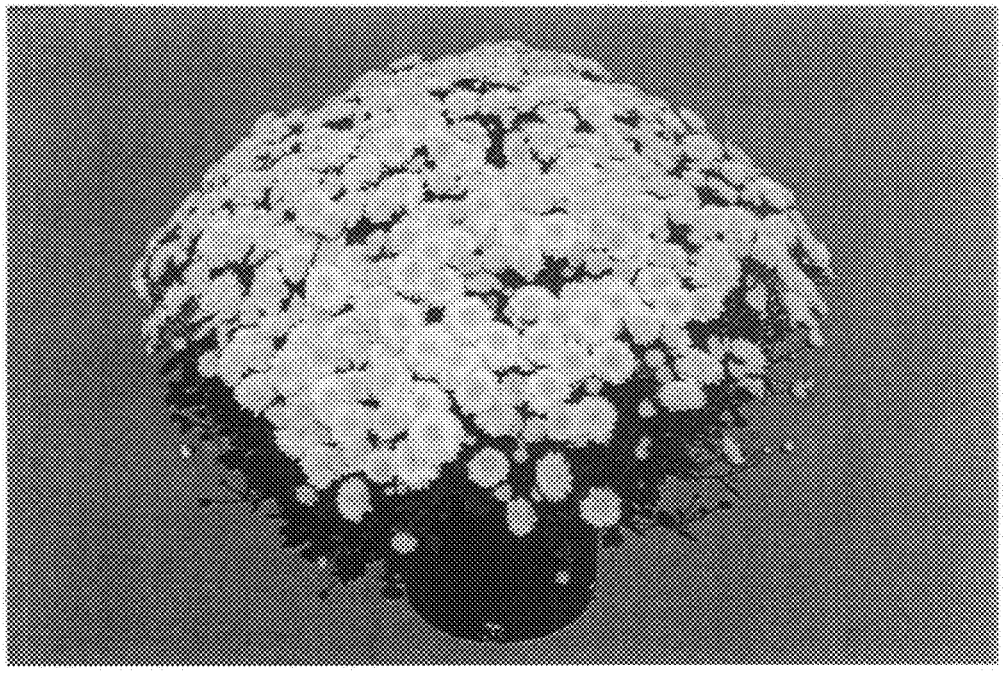
FIG. 1 shows a plant of the cultivar in full bloom.
Figure 2:
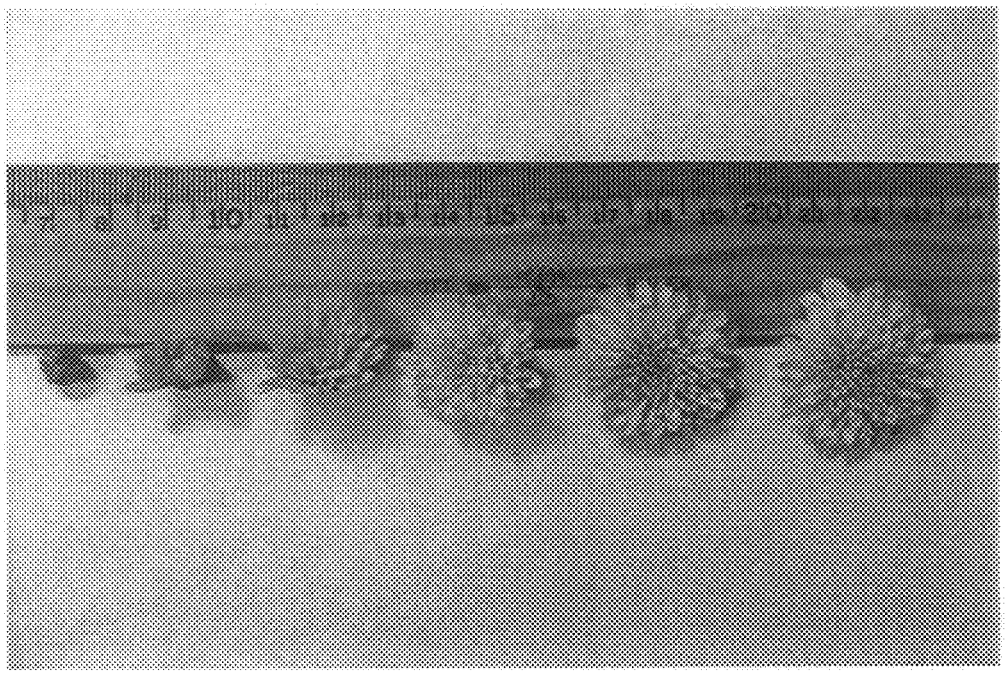
FIG. 2 shows the various stages of bloom of the new cultivar.
Figure 3:
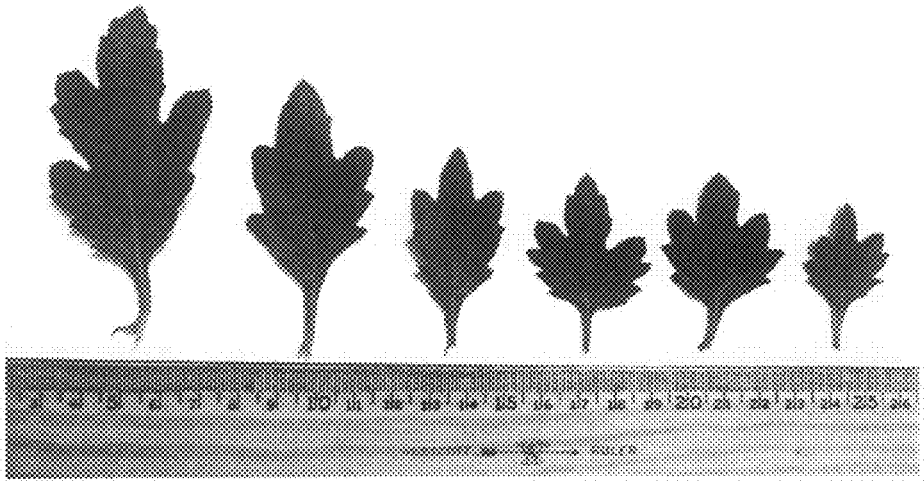
FIG. 3 shows the various stages of foliage of the new cultivar.

The observations and measurements were gathered from plants grown out door in DeMotte, Ind., USA, under natural day length and temperature and planted in week 25 in 2007. The natural blooming date of this crop was October 8 (week 41) . The average height of the plants was 30 cm. No growth retardants were used. No tests were done on disease or insect resistance or susceptibility. No tests were done on cold or drought tolerance. This new variety produces small sized blooms with yellow ray florets blooming for a period of 5 weeks.

From the cultivars known to inventor the most similar existing cultivar in comparison to 'Zanmugoldru' is 'Castor' (U.S. Plant Pat. No. 14,612). When 'Castor' and 'Zanmugoldru' are being compared the following difference is noticed: The difference of 'Castor' and 'Zanmugoldru' are (1) Flower size. And (2) Color flower center (1) The flowers of 'Castor' are larger in size than those of 'Zanmugoldru' (2) The flower center of 'Zanmugoldru' are more orange colored than those of 'Castor'.

The following is a description of the plant and characteristics that distinguish 'Zanmugoldru' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Botanical description of *chrysanthemum* plant named 'Zanmugoldru' | |
|---|---|
| Bud | |
| Size | Small; cross-section 0.1 cm, height 0.5 cm |
| Outside Color | Greyed-green 191A |
| Phyllaries | 3 rows |
| Phyllaries among disc-florets | Not present |
| Bloom | |
| Type | Double |
| Height | 1.4-1.7 cm |
| Size | 3.7-4 cm |
| Phyllary number | 20-24 |
| Phyllary color (upper surface) | Green 138A |
| Phyllary length and width | Length 8 mm, width 3 mm |
| Peduncle length | 9 cm |
| Peduncle color | Greyed green 191B |
| Number of blooms per branch | Approx. 7 blooms per branch |
| Duration of flowering | 5 weeks |
| Seeds | None observed |
| Fragrance | Typical *chrysanthemum*, slightly |
| Color | |
| Center of the flower | Immature stage: Yellow-orange 15A<br>Mature stage: Yellow-orange 15A |
| Color of upper surface of the ray-florets | Yellow 9A |
| Color of the lower surface of the ray-florets | Yellow 9A |
| Tonality from Distance | A garden mum with yellow flowers |
| Color of the ray-florets after aging of the plant | Yellow 9C |
| Ray florets | |
| Texture | Upper and under side smooth |
| Number | 240-250 |
| Cross-section | Flat |
| Longitudinal axis of majority | Straight |
| Length of corolla tube | 0.2-0.5 cm |
| Ray-floret margin | Entire |
| Ray-floret length | 1.3-1.7 cm |
| Ray-floret width | 0.4-0.5 cm |
| Ratio length/width | Medium |
| Shape of tip | Emarginate |
| Disc florets | Absent |
| Receptacle shape | Conical raised |
| Reproductive Organs | |
| Stamen | Absent |
| Pistil | One per ray-floret |
| Styles | Thin |
| Style color | Yellow-green 154C |
| Style Length | 0.3 cm |
| Stigma color | Yellow 3A |
| Stigma Width | 5 mm |
| Ovaries | Enclosed in calyx |

TABLE 1-continued

| Botanical description of *chrysanthemum* plant named 'Zanmugoldru' | |
|---|---|
| Plant | |
| Form | Grown as a spray type potmum, outdoor mounded and round |
| Growth habit | Raised mound |
| Growth rate | Medium to high |
| Height | 30 cm |
| Width | 50-55 cm |
| Stem Color | Greyed-brown 199A |
| Stem Strength | Strong |
| Stem Brittleness | Not brittle |
| Stem Anthocyanin Coloration | Not observed |
| Internode length | 1-5 cm |
| Length of lateral branch | From top to bottom 24-26 cm |
| Lateral branch color | Green 137C |
| Lateral branch, attachment | Strong |
| Branching (average number of lateral branches) | Prolific with 14-16 breaks after pinching |
| Natural season blooming date | October 8 (week 41) |
| Foliage | |
| Leaf color | Upper side: Green 147A<br>Lower side: Green 147C |
| Color midvein | Upper side: Green 137B<br>Lower side: Green 137B |
| Size | Small.; length 4-9 cm, width 2-4.5 cm |
| Quantity (number per lateral branch) | 18-20 |
| Shape | Elliptic |
| Texture upper side | Sparsely pubescent |
| Texture under side | Pubescent |
| Venation arrangement | Pinnate to palmate |
| Shape of the margin | Lobed |
| Shape of Base of Sinus Between Lateral Lobes | Rounded |
| Margin of Sinus Between Lateral Lobes | Diverging |
| Shape of Base | Cuneate to obtuse |
| Apex | Mucronate |
| Petiole length | 1-2 cm |
| Petiole color | Green 138A |

TABLE 2

| Differences with the comparison variety | | |
|---|---|---|
| | "Zanmugoldru" | 'Castor' |
| Flower size | 3.7-4 cm | 6.0-7.0 cm |
| Colour of flower center in mature stage | Yellow-orange 15A | Yellow 13B |

I claim:

1. A new and distinct variety of *chrysanthemum* plant 'Zanmugoldru' as described and illustrated.

* * * * *